US007846341B2

(12) United States Patent
Babaev

(10) Patent No.: US 7,846,341 B2
(45) Date of Patent: Dec. 7, 2010

(54) METHOD OF ULTRASONICALLY TREATING A CONTINUOUS FLOW OF FLUID

(75) Inventor: Eliaz Babaev, Minnetonka, MN (US)

(73) Assignee: Bacoustics, LLC, Minnetonka, MN (US)

( * ) Notice: Subject to any disclaimer, the term of this patent is extended or adjusted under 35 U.S.C. 154(b) by 1028 days.

(21) Appl. No.: 11/566,681

(22) Filed: Dec. 4, 2006

(65) Prior Publication Data
US 2008/0128362 A1    Jun. 5, 2008

(51) Int. Cl.
*C02F 1/36* (2006.01)
(52) U.S. Cl. .................................. 210/748.01; 422/22
(58) Field of Classification Search .................. 210/708, 210/748.01; 422/22
See application file for complete search history.

(56) References Cited

U.S. PATENT DOCUMENTS

| 3,708,263 | A | 1/1973 | Boucher |
| 4,086,057 | A | 4/1978 | Everett |
| 4,168,295 | A | 9/1979 | Sawyer |
| 4,211,744 | A | 7/1980 | Boucher |
| 4,599,459 | A | 7/1986 | Hirose |

(Continued)

FOREIGN PATENT DOCUMENTS

EP              424532 A4    12/1991

(Continued)

OTHER PUBLICATIONS

Constantinos Vassilakis, et al., Sonolysis of Natural Phenolic Compounds in Aqueous Solutions: Degradation Pathways and Biodegradability, Water Research, Jul. 2004, pp. 3110-3118, vol. 38—Issue 13, Dept. of Environmental Engineering, Technical University of Crete, Polytechneioupolis, Chania, Greece.

(Continued)

*Primary Examiner*—Walter D Griffin
*Assistant Examiner*—Cameron J Allen

(57) ABSTRACT

The present invention relates to a method of utilizing ultrasonic waves emitted into a fluid to treat the fluid, matter within the fluid, and/or organisms within the fluid in a variety of manners such as, but not limited to, cleaning objects within the fluid, sterilizing the fluid and/or objects within it, separating bonded matter within the fluid, segregating matter within the fluid into discrete laminas, killing organisms within the fluid, inactivating organisms within the fluid, extracting matter from organisms within the fluid, extracting matter from other matter within the fluid, inducing chemical reactions within the fluid, and/or converting toxic matter within the fluid into a less toxic state. The method of the present invention comprises the steps of flowing the fluid to be treated, which may contain matter and/or organisms to be treated, through an object or plurality of objects such as, but not limited to a pipe, emptying the fluid flowing through the first object into an second object or plurality of second objects such as, but not limited to, a tank, wherein each second object possesses a cross-sectional area larger than the opening between the first objects and second objects, emitting ultrasonic waves into the fluid that are not parallel to the primary flow of fluid through the second objects as it flows through the second objects, establishing laminar flow in the fluid as the fluid flows through the second objects, and collecting the fluid in a third object or plurality of third objects such as, but not limited to, pipes.

6 Claims, 1 Drawing Sheet

U.S. PATENT DOCUMENTS

Figure 1:
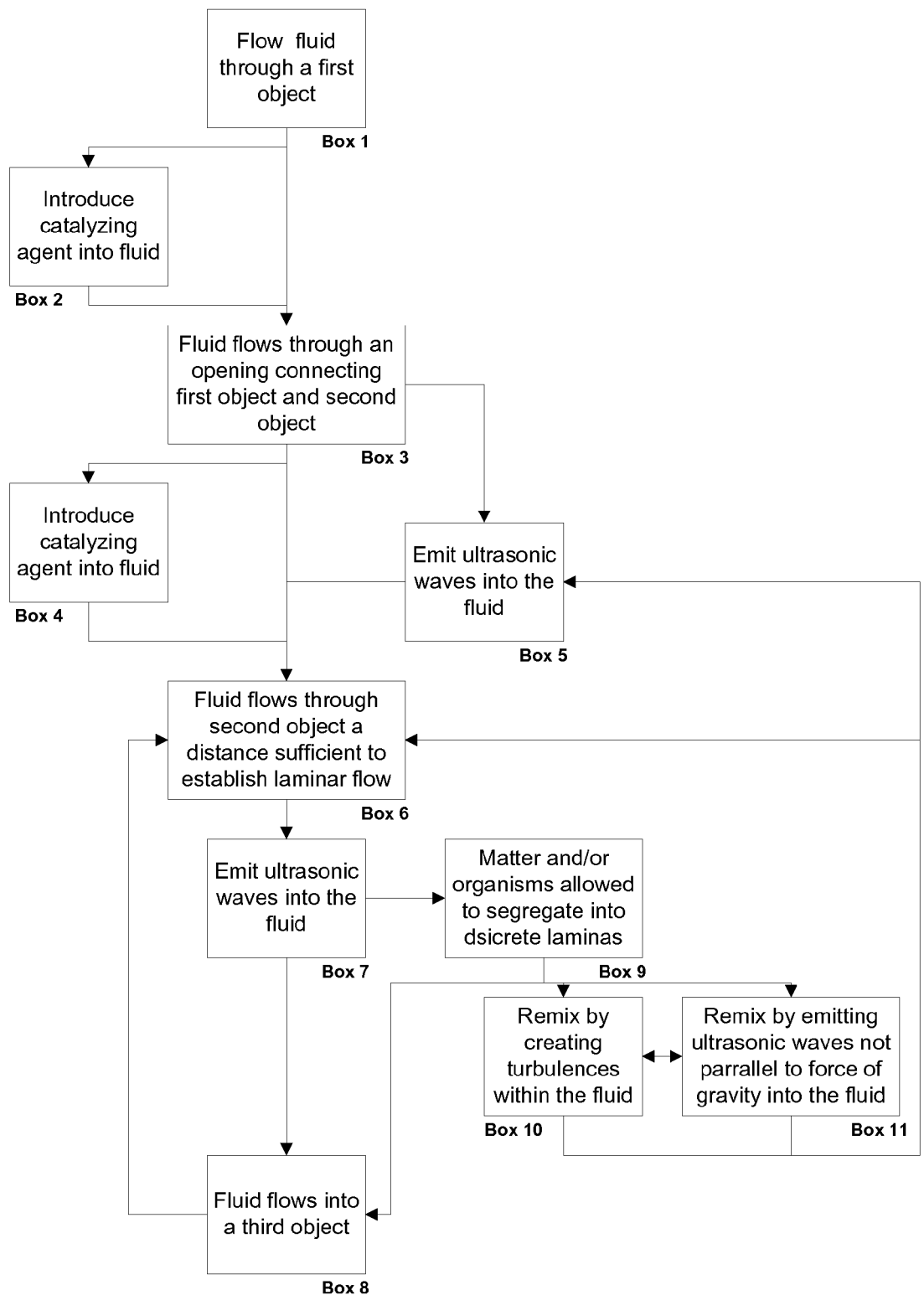

| | | | |
|---|---|---|---|
| 4,747,920 | A | 5/1988 | Muralidhara et al. |
| 5,076,266 | A | 12/1991 | Babaev |
| 5,124,050 | A | 6/1992 | Ushimaru et al. |
| 5,611,993 | A * | 3/1997 | Babaev ................... 422/20 |
| 5,658,534 | A | 8/1997 | Desborough et al. |
| 5,679,257 | A | 10/1997 | Coate et al. |
| 5,738,824 | A | 4/1998 | Pfeifer |
| 5,779,985 | A | 7/1998 | Sucholeiki |
| 5,783,790 | A | 7/1998 | Mitsumori et al. |
| 5,807,521 | A | 9/1998 | Franetzki |
| 5,876,671 | A | 3/1999 | Beugelsdijk et al. |
| 5,876,677 | A | 3/1999 | Mensinger et al. |
| 5,951,456 | A | 9/1999 | Scott |
| 5,958,228 | A | 9/1999 | Tokushima et al. |
| 6,214,222 | B1 | 4/2001 | Gerber |
| 6,228,273 | B1 | 5/2001 | Hammonds |
| 6,245,207 | B1 | 6/2001 | Yasuda et al. |
| 6,395,096 | B1 | 5/2002 | Madanshetty |
| 6,402,965 | B1 | 6/2002 | Sullivan et al. |
| 6,444,176 | B1 | 9/2002 | Yoshinaga et al. |
| 6,478,754 | B1 | 11/2002 | Babaev |
| 6,533,803 | B2 | 3/2003 | Babaev |
| 6,547,935 | B2 | 4/2003 | Scott |
| 6,569,099 | B1 | 5/2003 | Babaev |
| 6,601,581 | B1 | 8/2003 | Babaev |
| 6,623,444 | B2 | 9/2003 | Babaev |
| 6,649,069 | B2 | 11/2003 | DeAngelis |
| 6,663,554 | B2 | 12/2003 | Babaev |
| 6,723,064 | B2 | 4/2004 | Babaev |
| 6,761,729 | B2 | 7/2004 | Babaev |
| 6,827,844 | B2 | 12/2004 | Gunnerman |
| 6,858,181 | B2 | 2/2005 | Aoyagi |
| 6,878,288 | B2 | 4/2005 | Scott |
| 6,911,153 | B2 | 6/2005 | Minter |
| 6,929,750 | B2 | 8/2005 | Laurell et al. |
| 6,960,173 | B2 | 11/2005 | Babaev |
| 6,964,647 | B1 | 11/2005 | Babaev |
| 7,018,546 | B2 | 3/2006 | Kurihara et al. |
| 7,101,485 | B2 | 9/2006 | Dubruque et al. |
| 2001/0053384 | A1 | 12/2001 | Greenleaf et al. |
| 2002/0082666 | A1 | 6/2002 | Babaev |
| 2002/0088705 | A1 | 7/2002 | Scott |
| 2002/0103448 | A1 | 8/2002 | Babaev |
| 2002/0138036 | A1 | 9/2002 | Babaev |
| 2002/0156400 | A1 | 10/2002 | Babaev |
| 2002/0159917 | A1 | 10/2002 | Swart et al. |
| 2002/0190136 | A1 | 12/2002 | Babaev |
| 2002/0195402 | A1 | 12/2002 | Minter |
| 2003/0019791 | A1 | 1/2003 | Austin |
| 2003/0042174 | A1 | 3/2003 | Austin |
| 2003/0051988 | A1 | 3/2003 | Gunnerman et al. |
| 2003/0051989 | A1 | 3/2003 | Austin |
| 2003/0153961 | A1 | 8/2003 | Babaev |
| 2003/0171701 | A1 | 9/2003 | Babaev |
| 2003/0183798 | A1 | 10/2003 | Benje |
| 2003/0229304 | A1 | 12/2003 | Babaev |
| 2003/0234173 | A1 | 12/2003 | Minter |
| 2003/0236560 | A1 | 12/2003 | Babaev |
| 2004/0030254 | A1 | 2/2004 | Babaev |
| 2004/0042936 | A1 | 3/2004 | Ido |
| 2004/0069717 | A1 * | 4/2004 | Laurell et al. ............... 210/748 |
| 2004/0079680 | A1 | 4/2004 | Gunnerman |
| 2004/0129643 | A1 | 7/2004 | Dubruque et al. |
| 2004/0159537 | A1 | 8/2004 | Maeda et al. |
| 2004/0186384 | A1 | 9/2004 | Babaev |
| 2004/0256213 | A1 | 12/2004 | Marhasin et al. |
| 2005/0015024 | A1 | 1/2005 | Babaev |
| 2005/0220665 | A1 | 10/2005 | Ding |
| 2006/0025716 | A1 | 2/2006 | Babaev |
| 2006/0058710 | A1 | 3/2006 | Babaev |
| 2006/0086604 | A1 | 4/2006 | Puskas |
| 2007/0016110 | A1 | 1/2007 | Babaev |
| 2007/0031611 | A1 | 2/2007 | Babaev |
| 2007/0051307 | A1 | 3/2007 | Babaev |
| 2007/0088217 | A1 | 4/2007 | Babaev |
| 2007/0088245 | A1 | 4/2007 | Babaev |
| 2007/0088386 | A1 | 4/2007 | Babaev |
| 2007/0185527 | A1 | 8/2007 | Babaev |
| 2007/0231346 | A1 | 10/2007 | Babaev |
| 2007/0233054 | A1 | 10/2007 | Babaev |
| 2007/0239250 | A1 | 10/2007 | Babaev |
| 2007/0244528 | A1 | 10/2007 | Babaev |

FOREIGN PATENT DOCUMENTS

| | | |
|---|---|---|
| EP | 416106 A4 | 3/1992 |
| EP | 1370321 A1 | 12/2003 |
| EP | 1322275 A4 | 10/2004 |
| EP | 1526825 A1 | 5/2005 |
| EP | 1596940 A1 | 11/2005 |
| EP | 1617910 A1 | 1/2006 |
| EP | 1355696 A4 | 5/2006 |
| WO | 9005008 A1 | 5/1990 |
| WO | 9011135 A1 | 10/1990 |
| WO | 9012655 A1 | 11/1990 |
| WO | 9707830 A1 | 3/1997 |
| WO | 9717933 A1 | 5/1997 |
| WO | 9722398 A1 | 6/1997 |
| WO | 9817584 A1 | 4/1998 |
| WO | 9908967 A1 | 2/1999 |
| WO | 0007941 A1 | 2/2000 |
| WO | 0224150 A3 | 3/2002 |
| WO | 02055131 A3 | 7/2002 |
| WO | 02055150 A3 | 7/2002 |
| WO | 02060525 A3 | 8/2002 |
| WO | 02028350 A8 | 10/2002 |
| WO | 02076547 A1 | 10/2002 |
| WO | 02085456 A1 | 10/2002 |
| WO | 2004012859 A1 | 2/2004 |
| WO | 2004014284 B1 | 7/2004 |
| WO | 2004089469 A1 | 10/2004 |
| WO | 2004091722 A1 | 10/2004 |
| WO | 2006084308 A1 | 8/2006 |
| WO | 2007002598 A3 | 1/2007 |
| WO | 2007018980 A3 | 2/2007 |
| WO | 2007021427 A3 | 2/2007 |
| WO | 2007046989 A3 | 4/2007 |
| WO | 2007046990 A2 | 4/2007 |
| WO | 2007117800 A2 | 10/2007 |
| WO | 2007117964 A2 | 10/2007 |
| WO | 2007121123 A2 | 10/2007 |

OTHER PUBLICATIONS

Hugo Destaillats, et al., Scale-Up of Sonochemical Reactors for Water Treatment, Ind. Eng. Chem. Res., 2001, pp. 3855-3860, vol. 40, W. M. Keck Labs., California Institute of Technology, Pasadena, California, USA and Ultrasonic Energy Systems Inc., Panama City, FL, USA.

Sridevi Goskonda, et al., Sonochemical Degradation of Aromatic Organic Pollutants, Waste Management, 2002, pp. 351-356, vol. 22, Dept. of Chemistry, University of Louisiana at Monroe, LA, USA and Lab for Ecological Chemistry, Louisiana State University, Baton Rouge, LA, USA.

Weihua Song, et al., Ultrasonically Induced Degradation of 2-methylisoborneol and Geosmin, Water Research, 2007, pp. 2672-2678, vol. 41, Dept. of Chemistry and Biochemistry, Florida Int'l University, University Park, Miami, FL, USA.

Jun Liang, et al., Improvement in Sonochemical Degradation of 4-chlorophenol by Combined Use of Fenton-like Reagents, Ultrasonics Sonochmistry, 2007, pp. 201-207, vol. 14, Graduate School of Env. Studies, Tohoku University, Sendai, Japan and Inst. of Multidisciplinary Research for Advanced Materials (IMRAM), Tohoku University, Sendai, Japan.

A. Keck, et al., Influence of Particles on Sonochemical Reactions in Aqueous Solutions, Ultrasonics, 2002, pp. 661-665, vol. 40, Institut fur Technische Chemie, Karlsrue, Germany.

F. Javier Benitez, Simultaneous Photodegradation and Ozonation Plus UV of Phenolic Acids—Major Pollutants in Agro-Industrial Wastewaters, J. Chem. Technol. Blotechnol. 1997, pp. 253-260, vol. 70, Dept. of Chemical Engineering and Energy, University of Extremadura, Badajoz, Spain.

R. Rajan, et al., Modeling of Sonochemical Decomposition of CCl4 in Aqueous Solutions, Environ. Sci. Technol., 1998, pp. 1128-1133, vol. 32, Dept. of Chemical Engineering, Indian Institute of Science, Bangalore, India.

EPA, Wastewater Technology Fact Sheet, Ultraviolet Disinfection, EPA, Sep. 1999, Office of Water, United States EPA, Washington, D.C.

\* cited by examiner

METHOD OF ULTRASONICALLY TREATING A CONTINUOUS FLOW OF FLUID

BACKGROUND OF THE INVENTION

The present invention relates to a method of treating a continuous flow fluid that may be used to degrade matter within fluids, remove matter from fluids, separate matter within a fluid by density, sterilize fluids, and/or degrade toxic chemicals within a fluid.

The method of the present invention may also be utilized to clean, sterilize, and/or deodorize objects submerged within a continuous flow of fluid.

Subjecting a fluid to ultrasonic waves enables various treatments of the fluid and objects or matter within the fluid. For instance, submerging objects within a fluid subjected to ultrasonic waves can clean the objects. Placing a piece of solid matter such as, but not limited to, a salt pellet within a fluid subjected to ultrasonic waves causes erosion of the solid matter. Furthermore, matter bonded together may be separated when placed within a fluid subjected to ultrasonic waves. Ultrasonic waves traveling within a fluid may also be utilized to separate matter within fluid into bands or laminas.

Emitting ultrasonic waves into a fluid induces cavitations, small bubbles, within the fluid and causes objects and/or matter within the fluid to vibrate. As the ultrasound waves pass through the fluid, cavitations are spontaneously formed within the fluid. Explosion of the cavitations creates tiny areas of high pressure within the fluid Releasing high pressure into the fluid, the explosions of the cavitations provide the energy needed to treat the fluid and objects or matter within the fluid. In addition to creating cavitations, ultrasound waves emitted into a fluid vibrate matter and/or objects within the fluid. As matter and/or objects within the fluid vibrate, bonds holding the matter together and/or bond holding matter to an object weaken and sheer.

Ultrasonic waves emitted into a fluid in which an object is submerged remove matter from the object, thereby cleaning the object. Methods of utilizing ultrasonic, waves emitted into a fluid to clean objects within the fluid are employed by the devices disclosed in U.S. Patent Publication 2006/0086604 AI, U.S. Patent Publication 2005/0220665 AI, and U.S. Pat. No. 6,858,181 B2.

Trapping energy within cavitations, releasing energy from the explosions of cavitations, and/or inducing vibrations within matter, ultrasonic waves emitted into a fluid sheer the bonds holding matter together such as, but not limited to, adhesive bonds, mechanical bonds, ionic bonds, covalent bonds, and/or van der Waals bonds, thereby separating the matter. Ultrasonic waves passing through the fluid induce vibrations in matter within the fluid. As the matter vibrates, the bonds holding the matter together begin to stretch and sheer weakening, if not breaking, the bonds. Furthermore, matter within and/or near an exploding cavitation is exposed to tremendous changes in pressure that weakens, if not breaks, the bonds. Eventually the bonds holding the matter together become so weakened and strained that they break releasing small pieces and/or molecules of the matter into the fluid. If the matter is comprised of several different substances, the different substances comprising the matter become separated and released into the fluid. Methods of utilizing ultrasonic waves emitted into a fluid to break up and/or separate matter within the fluid are employed by the devices described in U.S. Patent Publication 2003/0183798 AI, U.S. Patent Publication 2003/0051989 AI, and U.S. Pat. No. 6,228,273 BI.

After matter within a fluid has been separated by ultrasonic waves emitted into the fluid, the matter may segregate into laminas. Segregation of matter within the fluid into laminas is assisted by the ultrasonic waves emitted into the fluid. Striking the matter the ultrasonic waves cause the matter to move through the fluid and into a particular lamina. The particular lamina that matter segregates into is dependent upon, among other things, the density of the matter. Less dense matter such as, but not limited to, gases move towards the upper lamina within the fluid. The movement of gases towards the upper lamina is driven by the ultrasonic waves colliding with the gas molecules as well as the natural tendency of matter less dense than the fluid it is in to move out of the fluid. Denser matter such as, but not limited to, solids and dense fluids, fall out of the fluid. As with less dense matter, ultrasonic waves striking dense manner exert a force on the matter in the direction the ultrasonic waves are traveling through the fluid. However, the force exerted by the ultrasonic waves on dense matter is insufficient to overcome dense matter's natural tendency to sink within the fluid. Consequently, dense matter separated from lighter matter segregates in lower laminas within the fluid. Below the laminas comprising less dense matter and above the laminas comprising dense matter, laminas containing matter of an intermediate density may form. As with dense matter and less dense matter, ultrasonic waves striking matter of an intermediate density exert a force on the matter. Unlike with dense matter, the force exerted by ultrasonic waves bitted into the fluid on matter of an intermediate density counteracts in whole or in part the natural tendency of the intermediate dense matter to sink. The more dense the matter the less effective the ultrasonic waves are at counteracting the matter's tendency to sink. Consequently, the matter will segregate into laminas based on, among other things, the density of the matter. A method of utilizing ultrasonic waves emitted into fluid to separate matter within a fluid into laminas based on density is employed by the device disclosed in U.S. Pat. No. 6,929,750 B2.

The breaking of bonds with ultrasonic waves emitted into a fluid can also be utilized to kill and/or inactivate organisms within the fluid such as, but not limited to, bacteria, viruses, fungi, algae, and/or yeast. Separating the molecules making up an organism's cellular membranes vibrations and cavitations create holes within an organism's cellular membranes. Chemicals may enter and/or leave the organism's cytoplasm through the holes created in the cellular membranes causing the cell to lyse and/or become poisoned. In addition to disrupting cellular membranes, ultrasonic waves emitted into a fluid may also denature or otherwise damage molecules needed by the organism for survival. For example, by inducing a protein within an organism to vibrate ultrasonic waves emitted into a fluid containing the organism may cause the subunits comprising the protein to separate. Denaturing a protein renders the protein ineffective in its life sustaining role, thereby essentially removing the protein from the organism. Loss of the protein may inactivate the organism and/or eventually lead to the organism's death, if the protein is needed for survival. Methods of utilizing ultrasonic waves emitted into a fluid to inactivate and/or kill organisms are employed by the devices disclosed in U.S. Patent Publication 2003/0234173 AI, U.S. Pat. Nos. 7,018,546 82, and 6,444, 176 B1.

Though there are methods of utilizing ultrasonic waves emitted into a fluid to clean objects within the fluid, sterilize the fluid and/or objects within it, separate bonded matter within the fluid, segregate matter within the fluid into discrete laminas, and kill and/or inactivate organisms within the fluid, a method providing all of the these treatments on a large scale is lacking.

SUMMARY OF THE INVENTION

The present invention relates to a method of utilizing ultrasonic waves emitted into a fluid to treat the fluid, matter within the fluid, and/or organisms within the fluid in a variety of manners such as, but not limited to, cleaning objects within the fluid, sterilizing the fluid and/or objects within it, separating bonded matter within the fluid, segregating matter within the fluid into discrete laminas, killing organisms within the fluid, inactivating organisms within the fluid, extracting matter from organisms within the fluid, extracting matter from other matter within the fluid, inducing chemical reactions within the fluid, and/or converting toxic matter within the fluid into a less toxic state.

The method of the present invention comprises the steps of flowing the fluid to be treated, which may contain matter and/or organisms to be treated, through an object or plurality of objects such as, but not limited to a pipe, emptying the fluid flowing through the first object into an second object or plurality of second objects such as, but not limited to, a tank, wherein each second object possesses a cross-sectional area larger than the opening between the first objects and second objects, emitting ultrasonic waves into the fluid that are transverse or not parallel to the primary flow of fluid through the second objects as it flows through the second objects, establishing laminar flow in the fluid as the fluid flows through the second objects, and collecting the fluid in a third object or plurality of third objects such as, but not limited to, pipes.

The openings between the first objects feeding fluid into the second objects should, have a cross-sectional area smaller than that of the second objects. When the fluid to be treated enters second objects, the velocity of the fluid decreases while the overall rate of flow (volume of fluid passing through the first and second object and into the third object per unit time) remains constant. The reduced velocity of the fluid within the second objects increases the amount of treatment received by each volume of fluid passing through the second objects by increasing the amount of time the fluid, matter within the fluid, and/or organisms within the fluid are exposed to ultrasonic waves. The increased exposure to ultrasonic waves may help to increase the efficacy of the ultrasonic treatment.

In certain situations, it may be desirable to establish laminar flow in the fluid prior to exposing the fluid, matter within the fluid, and/or organisms within the fluid to ultrasonic waves. Establishing laminar flow in the fluid helps to ensure the creation of stable cavitations and/or ultrasonic waves within the fluid. Utilizing laminar flow to create stable cavitations and/or ultrasonic waves within the fluid may increase the efficacy of the treatment of the fluid, matter within the fluid, and/or organisms within the fluid by ultrasonic waves emitted into in the fluid. Creating a laminar flow in the fluid as the fluid flows through the second object entails allowing the fluid to flow a sufficient distance such that any turbulences created in the fluid from the fluid's entry into the second objects, the fluid's collision with obstructions within the second objects, and/or the fluid's collision with the walls of the second objects dissipate before the fluid exits the second object.

As to help establish laminar flow within the fluid prior to reaching the first element emitting ultrasonic waves into the fluid such as, but not limited to, a Langevin ultrasound transducer or a cymbal ultrasound transducer the first element emitting ultrasonic waves into the fluid within the second object, with respect to the flow of fluid through the second object, should be located at a distance from the point of the second object at which fluid enters from the first objects that is at least approximately equal to the greatest height of the openings of the first objects into the second objects. The length of the second objects with respect to the flow of fluid through the second objects should be at least approximately equal to twice the greatest height of the openings of the first objects into the second objects.

Determining if a particular configuration allows for the creation of a laminar flow of the fluid through the second objects can be determined by observing fluid flowing through the second objects. Observing fluid flow through a particular configuration can be accomplished by constructing a transparent mock up of the intended configuration. A fluid containing fine particles suspended within the fluid can then be flowed through the transparent mock up.

The elements emitting ultrasonic waves into the fluid that are not parallel to the primary flow, overall direction of flow, of fluid through the second objects may be located within any sidewall and/or similar structure the second objects may possess. A sidewall is any wall and/or similar structure of the second objects that is not orientated perpendicular to the primary flow of fluid through the second objects.

Any given element emitting ultrasonic waves into the fluid as the fluid flows through the second objects may emit ultrasonic waves of a particular frequency and/or amplitude or may emit ultrasonic waves varying in frequency and/or amplitude. The frequency of the ultrasonic waves emitted should be at least approximately 18 kHz. Preferably the ultrasonic waves emitted into the fluid as the fluid flows through the second objects possess a frequency between approximately 20 kHz and approximately 200 kHz or between approximately 1 MHz and approximately 5 MHz. The amplitude of the ultrasonic waves emitted into the fluid should be at least approximately 1 micron or greater.

Every volume of fluid passing through the second objects should be exposed to ultrasonic waves of each frequency and/or amplitude emitted into the fluid for at least one second. Preferably, every gallon of fluid to be treated should be exposed to ultrasonic waves of each frequency and/or amplitude emitted into the, fluid for approximately 5 seconds. A discrete element may be responsible for emitting ultrasonic waves of a particular frequency and/or amplitude or range of frequencies and/or amplitudes into the flowing fluid. Alternatively, the elements emitting ultrasonic waves into the fluid may be arranged such that fluid is exposed zones of ultrasonic waves of a particular frequency and/or amplitude or range of frequencies and/or amplitudes.

Creating zones of ultrasonic waves may be accomplished by arranging the ultrasonic emitting elements into bands and/or arrays of bands responsible for emitting ultrasonic waves of a particular frequency and/or amplitude or range of frequencies and/or amplitudes into the fluid. Arranging the elements responsible for emitting ultrasonic waves of a particular frequency and/or amplitude or range of frequencies and/or amplitudes into bands and/or arrays of bands helps enable the creation of stable cavitations and/or ultrasonic waves of the desired frequencies and/or amplitudes within the fluid as the fluid flows through the second objects.

The elements releasing ultrasonic waves into the fluid may be activated simultaneously. Alternatively, the ultrasound releasing elements, bands, and/or arrays of bands may be activated sequentially such that an element, band, and/or array is activated when the preceding transducer, band, and/or array, with respect to the flow of fluid, is deactivated. The elements emitting ultrasonic waves may be driven by a variety of wave patterns such as, but not limited to, square, triangle, trapezoidal, sinusoidal, and/or any combination thereof.

The intensity of the ultrasound energy released by the ultrasound emitting elements required to treat the fluid as the fluid flows through the second objects is dependent on the depth of the fluid above the emitting element. The intensity required for a particular depth can be determined by placing the desired depth of fluid over an emitting element. Ultrasound energy of an ever increasing intensity can then be emitted from the element while the surface of the fluid over the element is monitored. When the desired treatment of fluid is observed at the surface of the fluid, the intensity of the ultrasound energy released into the fluid should be noted and recorded, as it corresponds to the intensity required for the given depth of fluid. If the emitting elements are oriented such that the ultrasonic waves emitted into the fluid intersect at an angle less than 180 degrees, then the above procedure should be performed with a depth of fluid equal to the maximum distance from the emitting elements to the point of intersection of the ultrasonic waves. If the ultrasonic waves emitted into the fluid from multiple emitting elements intersect at a 180 degree angle, then the above procedure should be performed with a depth of fluid equal to half the distance between the emitting elements.

Emitting ultrasonic waves of varying frequencies and/or amplitudes helps to enable treatment of fluids containing various matter and/or organisms. As the fluid flows through the second object, a laminar flow may be established prior to reaching the first element emitting ultrasonic waves into the fluid. The ultrasonic waves emitted into the fluid induce cavitations within fluid and/or vibrations within any matter and/or organism within the fluid. The energy released by cavitations within the fluid and the vibrations, if any, induced within any matter and/or organism present in the fluid depends upon the frequency and/or amplitude of the ultrasonic waves passing through the fluid.

Different matter and/or organisms within fluid may be sensitive to ultrasonic waves of different frequencies and/or amplitudes. Exposing matter to ultrasonic waves of the proper frequency induces resonating vibrations within the matter. Resonating vibrations place the greatest amount of strain on the bonds within the matter, thereby making them more likely to break spontaneously and/or break when exposed to the energy released from the exploding cavitations. Likewise, the membranes and/or molecules of different organisms will vibrate in resonance when exposed to ultrasonic waves of a particular frequency and/or amplitude thereby making the organism's membranes more likely to rupture spontaneously and/or when exposed to the energy released from the exploding cavitations. Inducing resonating vibrations within the molecules of an, organism makes the organism's molecules more likely to denature spontaneously and/or when exposed to the energy released from the exploding cavitations.

As the cells and/or viruses within the fluid stream rupture, matter within the cells and/or viruses such as, but not limited to, proteins, nucleic acids, and/or sugars, are released into the fluid. Matter released from organisms within the fluid is then free to segregate into laminas. Segregation of material into different laminas of the fluid may be most efficient within regions of laminar fluid flow. Likewise, molecules released from the erosion of matter and/or from the breaking of bonds within the matter are free to segregate into laminas when separated. The laminas within the fluid may be collected with different third objects into which the fluid to be treated flows after leaving the second objects.

For example, it may be desirable to collect dense matter located within the lower laminas with an outlet pipe or similar collecting third objects located near the bottom of the second objects. The collected dense matter may be re-circulated through the second objects as to expose the matter to further treatment. Exposing the matter to several treatments within the second objects may allow more matter of a lesser density to be separated from the denser matter and/or segregate into higher laminas within the fluid. Less dense matter located within the upper laminas may be collected with an outlet pipe located near the top of the second object. Alternatively, volatile matter segregating a into the upper lamina of the fluid may be allowed to escape from the fluid through an open top of second objects and/or a porous material covering the second objects. Matter of an intermediate density segregating into middle laminas may be collected with an outlet pipe or similar collecting third objects located near the middle of the second objects. The fluid and/or laminas recovered from the second objects by the collecting third objects may be discharged and/or retained for further processing.

Disrupting the established laminar flow of fluid during treatment may be desirable. For instance disrupting laminar flow by creating turbulences such as, but not limited to, vortices, burbles, eddies, and/or any combination thereof may allow matter segregated into discrete laminas to be remixed. Matter within laminas not disturbed by the turbulences, however, will remain segregated. Combining matter from an upper lamina and a lower lamina may be accomplished by creating a vortex within the fluid. Spiraling downward, the vortices pull matter from laminas along the length of the vortices downward to lower laminas. Creating a vortex within the fluid as the fluid flows through the second objects can be accomplished by placing an outlet or plurality of outlets in the lower portion of the second objects.

Combining matter from adjacent laminas may be accomplished by creating eddies at the boundary of two or more laminas. The turbulence created by the eddy may pull matter from upper laminas into the lower laminas and matter from the lower laminas into the upper laminas. Creating an eddy at the upper and lower boundaries of a lamina may allow material from both lamina above and below to be pulled into the middle lamina. Eddies can be created by placing obstructions in the path of the fluid's flow through the second objects that the fluid cannot smoothly flow around such as, but not limited to, rectangular prisms and/or triangular prisms. Alternatively, material from several adjacent laminas may be combined by creating large burbles within the second objects that span several laminas. Creating a burble can be accomplished by placing an airfoil like structure in the path of the fluid that is angled with respect to the flow of fluid striking the airfoil. Turbulence disrupting laminar flow may also be created by injecting fluid into the second objects.

Remixing matter segregated into laminas may also be accomplished with ultrasonic waves emitted into the fluid. Emitting ultrasonic waves into the fluid that are transverse or not parallel to the force of gravity acting on the matter within the fluid may carry matter out of a lamina into which the matter has segregated and into other laminas. As ultrasonic waves not parallel to the force of gravity acting on the matter within the fluid pass through the fluid, the ultrasonic waves may direct matter within the fluid that is along the waves' path to anti-nodal points of the waves. If the ultrasonic waves not parallel to the force of gravity acting on the matter within the fluid span multiple laminas, then matter within one lamina may be carried to the laminas encompassing anti-nodal points of the wave. Emitting ultrasonic waves into the fluid that are not parallel to the force of gravity acting on matter within the fluid may be accomplished with ultrasonic emitting elements located within sidewalls or similar structures of the second objects and/or located within walls or similar structures of the second objects approximately perpendicular to the primary flow of fluid through the second objects.

Selectively mixing material segregated into laminas may be desirable if chemical reactions are to take place within the fluid. For instance, matter within the fluid may react to form a desired product. However, formation of the desired product may be hindered by the presence of other matter within the fluid. The other matter may be a separate reagent, a product of the reaction producing the desired product, and/or the desired product itself. The other matter may react with the reagents producing the desired product thereby preventing the production of the desired product. Alternatively, reacting with the desired product, the other matter may convert the desired product into an undesired product.

Segregating the reagents, desired product, and/or other matter into discrete laminas and then selectively recombining the laminas prevents other matter that hinders and/or prevents the formation of the desired product from reacting with the reagents producing the desired product and/or from reacting with the desired product. Similarly, segregating the reagents, desired product, and/or other matter into discrete laminas allows optimization of desired chemical reactions.

Thus, after a chemical reaction occurring within and/or outside the second objects, a laminar flow of fluid may be established within the fluid flowing through the second objects. The matter within the fluid may then be allowed to segregate into discrete laminas. Selectively remixing laminas containing matter that reacts to produce the desired product and/or another desired reaction may then be accomplished by creating turbulences within the fluid and/or remixing the lamina outside of the second objects. Following and/or during the selective remixing of the laminas, the matter within the combined laminas may then be allowed to react within and/or outside the second objects. Serially segregating, recombining, and/or reacting the matter within the fluid may be done with one configuration of first, second, and third objects and/or within several such configurations connected in series and/or in parallel.

Reactions occurring within the second objects may be catalyzed by a variety of catalyzing agents, such as, but not limited, chemicals, microorganisms, enzymes, radio waves, microwaves, light waves, and/or any combination thereof introduced into the fluid while and/or prior to the fluid flowing through the second objects. For instance, prior to the fluid entering the tank from the first objects, a chemical such as, but not limited to, chlorine, bromine, ozone, antibiotic, antifungal, antiviral, and/or any combination thereof, may be introduced into the fluid. The introduced chemical may react with fluid, with matter within the fluid, and/or with organism within the fluid as to bring about a desired result. For instance, the chemical may react with matter within the fluid as to transform the matter into a less toxic state. Alternatively, the chemical may react with organisms within the fluid as to kill and/or inactivate the organisms. The energy within and/or released from cavitations within the fluid and/or vibrations of matter and/or organisms within the fluid may increase the efficacy and/or rate of the chemical reaction.

Accordingly, one aspect of the present invention to may be to provide a method of cleaning objects submerged in a flowing fluid.

Another aspect of the present invention may be to provide a method of sterilizing objects submerged in a flowing fluid.

Another aspect of the present invention may be to provide a method of deodorizing objects submerged in a flowing fluid.

Another aspect of the preset invention may be to provide a method of sterilizing a flowing fluid flowing.

Another aspect of the present invention may be to provide a method of inactivating organisms within a flowing fluid.

Another aspect of the present invention may be to provide a method of killing organisms within a flowing fluid.

Another aspect of the present invention may be to provide a method of deodorizing a flowing fluid.

Another aspect of the present invention may be to provide a method of separating bonded matter within a flowing fluid.

Another aspect of the present invention may be to provide a method of releasing matter within organisms within a flowing fluid.

Another aspect of the present invention may be to provide a method of segregating matter within a flowing fluid flowing into laminas.

Another aspect of the present invention may be to provide a method of converting toxic matter within a flowing fluid into a less toxic state.

Another aspect of the present invention may be to provide a method of removing gases from the flowing fluid.

Another aspect of the present invention may be to provide a method of extracting matter from a combination of matter within a flowing fluid.

Another aspect of the present invention may be to provide a method of extracting matter from cells within a flowing fluid.

Another aspect of the present invention may be to provide a method of extracting matter from viruses with a flowing fluid.

These and other aspects of the invention will become more apparent from the written description and figures below.

BRIEF DESCRIPTIONS OF THE DRAWINGS

The present invention will be shown and described with reference to the drawings of preferred embodiments and clearly understood in detail.

FIG. 1 depicts a flow chart illustrating some of the possible embodiments of the method of the present invention.

DETAILED DESCRIPTION OF THE INVENTION

FIG. 1 is a flow chart depicting possible embodiments of the method of the present invention. The method begins, as indicated by Box 1, by flowing a fluid to be treated through a it object such as, but not limited to an inlet pipe. The fluid to be treated then flows through an opening connecting the first object and a second object, as indicated by Box 3, wherein the second object possesses a cross-sectional area greater than that of the opening between the first object and second object such as a tank. Laminar flow is then established within the fluid by allowing the fluid to flow through the second object a sufficient distance such that any turbulence within the fluid dissipates, as indicated by Box 6. Establishing laminar flow in the fluid after the fluid enters the second object can be accomplished by allowing the fluid to flow a distance at least approximately equal to the greatest height of the opening connecting the first object to the second object. Placing the opening of the first object at or near the base of the second object may further assist in establishing laminar flow. Before leaving the second object, the fluid is exposed to ultrasonic waves that are transverse or not parallel to the primary flow of fluid through the second object, as indicated by Box 7. The ultrasonic waves emitted into the fluid may be a particular amplitude and/or frequency or range of amplitudes and/or frequencies. With respect to the latter, as fluid flow through the tank it may pass through discrete zones in which ultrasonic waves of a particular amplitude and/or frequency or ultrasonic waves ranging in amplitude and/or frequency are emitted into the fluid. The fluid, then flows from the second object into a third object such as, but not limited to an outlet pipe, as indicated by Box 8, from which it may collected and/or re-circulated through the second object. Before entering the third the object, the fluid should travel a distance with the second object at least approximately equal to twice the greatest height of the opening between first object and second object.

In some situations, it may be desirable to emit ultrasonic waves into regions of the fluid not in laminar flow within the second object, as indicated by Box 5.

In keeping with FIG. 1, before the fluid enters the second object, an agent catalyzing the intended treatment of the fluid such as, but not limit to, chlorine, ozone, peroxide, ultraviolet light, an enzyme, and/or an organism may be introduced into the fluid, as indicated by Box 2. Alternatively and/or in addition to, a catalyzing agent may be introduced into the fluid as it flows through the second object, as indicated by Box 4.

Prior to the fluid exiting the second object, the matter and/or organism within the fluid may be allowed to segregate into discrete laminas, as indicated by Box 9. Laminas containing the segregated matter may then be collected by the third object oriented with respect to the second object such that the intended laminas to be collected flow into the third object. Alternatively, the segregated matter and/or organisms may be remixed by creating turbulences within the fluid, as indicated by Box 10. Alternatively, the segregated matter and/or organisms may be remixed by emitting ultrasonic waves into the fluid that are not parallel to the force of gravity acting on the matter and/or organism within the fluid, as indicated by Box 11. The fluid may then be re-exposed to ultrasonic waves and/or allowed to flow a sufficient distance such that laminar flow, if destroyed, is allowed to be reestablished in the fluid.

Ensuring the proper flow of fluid through the second object may be accomplished by, setting the aggregate pressure of fluid entering the second object equal to the aggregate pressure of the fluid exiting second object.

Positioning the opening the first object into the second object directly opposite the opening of the second object into the third object may assist in establishing the proper flow of fluid through the second object. A device employing the method of the present invention is disclosed in U.S. patent application Ser. No. 11/562,343, filed Nov. 21, 2006, the teachings of which are hereby incorporated by reference.

Although specific embodiments have been illustrated and described herein, it will be appreciated by those of ordinary skill in the art that any arrangement that is calculated to achieve the same or similar purpose may be substituted for the specific embodiments disclosed. It is to be understood that the above description is intended to be illustrative and not restrictive. Alternative combinations of the step of the disclosed embodiments and other embodiments will be apparent to those having skill in the art upon review of the present disclosure. The scope of the present invention should be determined with reference to the appended claims, along with the full scope of equivalents to which such claims are entitled.

The method of action of the present invention and prior art devices presented herein are based solely on theory. They are not intended to limit the method of action of the present invention or exclude of possible methods of action that may be present within the present invention and/or responsible for the actions of the present invention.

I claim:

1. A method for treating a fluid comprising the steps of:
    delivering the fluid through an inlet into a tank;
    establishing a laminar flow region within the tank;
    locating at least one ultrasound transducer within a sidewall of the tank;
    establishing laminas within the laminar flow region;
    emitting ultrasonic waves at a frequency and an amplitude into the laminar flow region from the ultrasound transducer;
    cavitating the fluid within the laminas; and
    varying the depth of the fluid within the tank.

2. A method for treating a fluid comprising the steps of
    delivering the fluid through an inlet pipe into a tank;
    establishing a laminar flow region within the tank;
    locating at least one ultrasound transducer within a sidewall of the tank;
    establishing laminas within the laminar flow region;
    emitting ultrasonic waves at a frequency and an amplitude into the laminar flow region from the ultrasound transducer;
    cavitating the fluid within the laminas; and
    separating and recirculating a dense matter lamina.

3. The method of claim 1 also having the additional step of collecting a gas product.

4. The method of claim 1 also having a step of remixing at least two laminas.

5. The method of claim 1 further comprising passing the fluid through a plurality of zones with each zone having the ultrasound transducer providing a different amplitude.

6. The method of claim 1 further comprising passing the fluid through a plurality of zones with each zone having the ultrasound transducer providing a different frequency.

* * * * *